United States Patent [19]

Welstead, Jr. et al.

[11] 4,151,285
[45] Apr. 24, 1979

[54] 1,5-DISUBSTITUTED-1,2-DIHYDRO-2H-1,4-BENZODIAZEPIN-2-ONES

[75] Inventors: William J. Welstead, Jr.; Robert F. Boswell, Jr., both of Richmond, Va.

[73] Assignee: A. H. Robins Company, Inc., Richmond, Va.

[21] Appl. No.: 905,268

[22] Filed: May 12, 1978

[51] Int. Cl.² .................. C07D 243/24; A61K 31/55
[52] U.S. Cl. .............................. 424/267; 260/239.3 D
[58] Field of Search ................ 260/239.3 D; 424/267

[56] References Cited

U.S. PATENT DOCUMENTS 3,542,769  11/1970  Kaiser et al. .................. 260/239.3 D
3,641,002  2/1972  Yamamoto et al. ........... 260/239.3 D

*Primary Examiner*—Natalie Trousof
*Assistant Examiner*—Robert T. Bond

[57] ABSTRACT

1,5-Disubstituted-1,2-dihydro-2H-1,4-benzodiazepin-2-ones of the formula

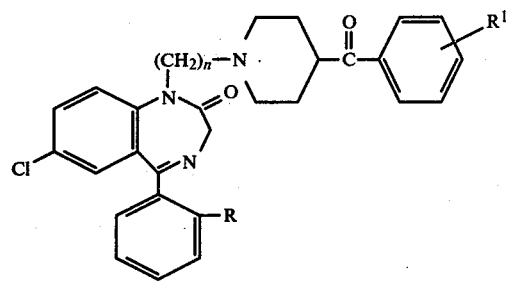

wherein R is hydrogen or fluoro, $R^1$ is hydrogen, fluoro chloro, bromo or trifluoromethyl, and n is 2 to 4, having anticonvulsant activity and useful as anti-anxiety agents, are disclosed.

12 Claims, No Drawings

1,5-DISUBSTITUTED-1,2-DIHYDRO-2H-1,4-BENZODIAZEPIN-2-ONES

BACKGROUND OF THE INVENTION

1. Field of the Invention

The present invention is concerned with 1,5-disubstituted-1,2-dihydro-2H-1,4-benzodiazepin-2-ones and is more particularly concerned with 5-phenyl-1-[ω-(benzoylpiperidino)alkyl]-7-chloro-1,2-dihydro-2H-1,4-benzodiazepin-2-ones, compositions containing the same as active ingredients and methods of making and using the same.

2. Discussion of the Prior Art

The prior art literature including patents, scientific articles, preliminary reports and papers presented at symposia, discloses numerous 1,5-disubstituted-1,4-benzodiazepin-2-ones. Among those which can be cited are U.S. Pat. Nos. 3,136,815; 3,109,843; 3,371,085; 3,236,838; and 3,391,138; Cutting's Handbook of Pharmacology, pgs. 585–587, 5th Ed. Meredith Corporation, New York, New York, Zbinden and Randall, Pharmacology of Benzodiazepines in Advances in Pharmacology, Vol. 5, 1967 (Academic Press) and in the paper by Sternback and Randall, "Some Aspects of Structure — Activity Relationship in Psychotropic Agents of the 1,4-Benzodiazepine Series," pgs. 53–69, presented at a Symposium at the Regional Research Laboratory, Hyderbad, India. *CSIR,* New Delhi, India (1966).

SUMMARY OF THE INVENTION

The novel concept of the present invention resides in the provision of novel 1,5-disubstituted-1,2-dihydro-2H-1,4-benzodiazepin-2-ones having a benzoylpiperidinoalkyl radical in the 1-position of the benzodiazepin-2-one nucleus. The compounds have anticonvulsant activity against electrical and chemical induced convulsions.

The novel compounds of the present invention have the general Formula I:

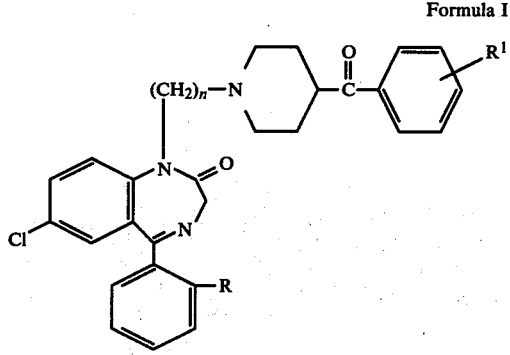

Formula I wherein;
R represents hydrogen or fluoro,
$R^1$ represents hydrogen, fluoro, bromo, chloro or trifluoromethyl,
n is a positive integer from 2–4 inclusive.

The non-toxic pharmaceutically acceptable acid addition salts of Formula I are within the purview of the present invention.

The present invention contemplates various embodiments as can be seen from Formula I and the respective values assigned to the symbols R, $R^1$ and n.

In one embodiment of the present invention the value of n can be 2 through 4 inclusive; R and $R^1$ are hydrogen, while in another embodiment n can be 2 through 4 inclusive; and R, and $R^1$ are both fluorine.

Another embodiment of the invention contemplates compounds wherein n is 3, R is fluorine and $R^1$ is chloro or fluoro.

A preferred embodiment of the present invention is the compound wherein R is fluorine and the group attached to the 1-position is the 3-[4-(p-fluorobenzoyl)-piperidino]propyl radical.

Chemical compounds which possess good anticonvulsant properties are generally useful as anti-anxiety agents, e.g., diazepin.

Anticonvulsant properties are determined using groups of five adult female mice. The mice are given 50 and 150 mg/kg. i.p. of a test drug 30 minutes prior to electrical or chemical challenge.

Animals are challenged electrically by placing brass electrodes on the corneas and applying an electrical stimulus (60 Hz., 5 msec. pulse width, 34 mA intensity) for 0.2 seconds by way of a Grass Stimulator and constant current unit and a Hunter Timer. The absence of tonic seizures upon cessation of the stimuli is scored as protection in that animal. The number of animals protected from tonic seizures at each dose is determined.

For chemical challenge, each animal receives a convulsant dose of pentylenetetrazole (120 mg/kg., i.p.). Complete suppression of tonic seizures of death during the next hour is scored as protection in that animal.

In both electrical and chemical challenge when a test drug exhibits good activity, protective $ED_{50}$ values are determined (Litchfield and Wilcoxon, 1949) using additional animals with geometrically-spaced doses.

When tested according to the foregoing procedure the compound of Example 1 had a protective $ED_{50}$ of 6.8 (5.1–9.2) against electroshock-induced convulsions and a protective $ED_{50}$ of 4.3 (2.5–7.2) against pentylenetetrazole-induced convulsions.

It is, therefore, an object of the present invention to provide novel 5-phenyl-1-[ω-(benzoylpiperidino)alkyl]-7-chloro-1,2-dihydro-2H-1,4-benzodiazepin-2-ones. A further object is to provide novel 5-phenyl-1-[ω-(benzoylpiperidino)alkyl]-7-chloro-1,2-dihydro-2H-1,4-benzodiazepin-2-ones having anti-convulsant activity and useful as anti-anxiety agents. A still further object is to provide methods for producing the novel compounds, pharmaceutical compositions containing said compounds as active ingredients and methods for the utilization thereof. Additional objects will be apparent to one skilled in the art and still other objects will be apparent hereinafter.

The term "phenyl" whenever used in the specification and the appended claims refers to the unsubstituted phenyl radical and to the monosubstituted phenyl radical wherein the substituent is fluoro, chloro, bromo or trifluoromethyl. The term "benzoyl" has the formula —C(O)-phenyl.

The compounds of the invention are preferably employed in the form of non-toxic pharmaceutically acceptable acid addition salts. Appropriate pharmaceutically acceptable acid addition salts are those derived from inorganic acids such as hydrochloric, hydrobromic, sulfuric and phosphoric, and organic acids such as acetic, citric, lactic, maleic, oxalic, fumaric and tartaric. The preferred addition salts are the hydrochloride, maleate, fumarate and oxalate. The acid addition salts of the product compounds are conventionally prepared by reaction of the basic compounds with the acid, either or both of which may be in the form of ether, alcohol or acetone solutions.

DETAILED DESCRIPTION OF THE INVENTION

The novel compounds of Formula I may be prepared by contacting a 5-phenyl-7-chloro-1,2-dihydro-2H-1,4-benzodiazepin-2-one (II) with an ω-(4-benzoylpiperidino)alkyl halide (III) according to the following reaction scheme:

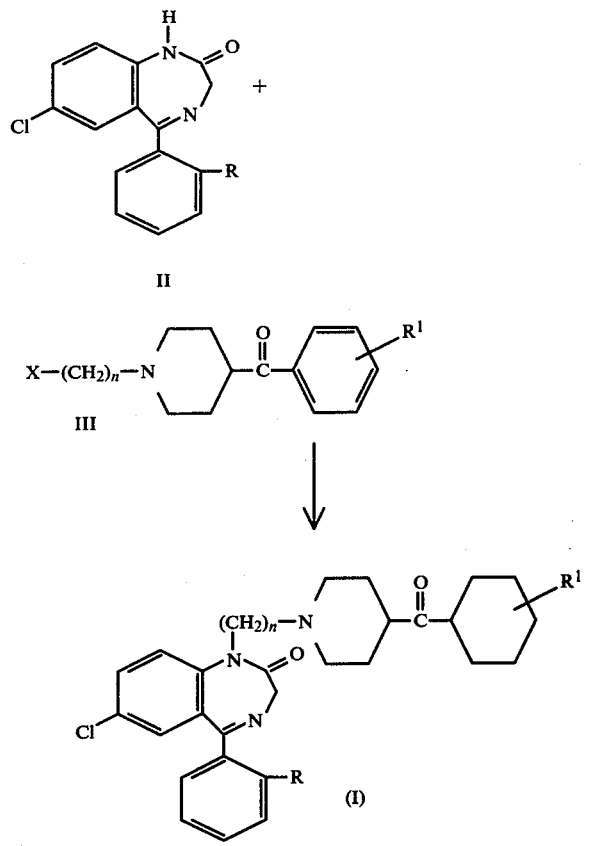

wherein R, $R^1$ and n have the values hereinabove assigned, and X is a halide radical, preferably chloride.

Generally speaking, a solution of a 5-phenyl-7-chloro-1,2-dihydro-2H-1,4-benzodiazepin-2-one (II) in a dry solvent such as dimethylformamide is added dropwise to a stirring suspension of sodium hydride (50% dispersion in oil) in the same solvent, the reaction system being protected from moisture by suitable means at a pot temperature of from about 20°–30° C. After stirring for a period of from about one hour to about 4 hours at 20°–30° C., the pot temperature is raised to from about 45° C. to about 55° C. for a period of from about one-quarter hour to about one hour. A solution of an ω-(benzoylpiperidino)alkyl halide (III) in the same solvent is added dropwise to the reaction mixture with stirring for an additional period of from about 15 hours to about 24 hours at 20°–30° C. to complete the reaction. Water is added to the reaction mixture to decompose excess sodium hydride and the product is isolated by an appropriate physical-chemical procedure.

In the foregoing general procedure an alkali amide as, for example, sodium amide, can be conveniently used to metallate the nitrogen atom of the 5-phenyl-7-chloro-1,2-dihydro-2H-1,4-benzodiazepin-2-one. Additionally, the reaction time can be shortened by increasing the pot temperature to from about 60° C. to about 110° C.

The 5-phenyl-7-chloro-2H-1,4-benzodiazepin-2-ones (II) are known to the art and can be readily prepared by the methods such as those disclosed in U.S. Pat. No. 3,136,815.

The ω-(4-benzoylpiperidino)alkyl halides (III) and procedures for making them are disclosed in Preparations 1-9.

PREPARATION 1

1-Acetyl-4-(p-fluorobenzoyl)piperidine

A mixture of 93 g. (0.7 mole) of aluminum chloride in 150 ml. of fluorobenzene was stirred while 70 g. (0.37 mole) of 1-acetylisonipecotic acid chloride was added in small portions. After the addition was complete, the mixture was refluxed for one hour. The mixture was poured onto ice and the two layers separated. The aqueous layer was extracted twice with chloroform and the chloroform extracts were added to the organic layer. The organic solution was dried over anhydrous sodium sulfate and filtered. The filtrate was concentrated and 73.7 g. (80%) of 1-acetyl-4-(p-fluorobenzoyl)piperidine was obtained as a crystalline residue. Recrystallization from ligroin-isopropyl ether gave a white crystalline product melting at 75°–78° C.

Analysis: Calculated for $C_{14}H_{16}FNO_2$: C, 67.45; H, 6.47; N, 5.62; Found: C, 67.26; H, 6.50; N, 5.54.

PREPARATION 2

4-(p-Fluorobenzoyl)piperidine Hydrochloride

A solution of 70.6 g. (0.27 mole) of 1-acetyl-4-(p-fluorobenzoyl)piperidine in 200 ml. of 6N hydrochloric acid was refluxed for 2 hours. The cooled solution was extracted twice with ether. The aqueous solution was made basic and extracted with benzene. The benzene extracts were dried over anhydrous sodium sulfate and concentrated. The oily residue weighed 38.2 g. (69%). The hydrochloride salt was prepared and recrystallized from isopropanol giving a crystalline solid melting at 222°–224° C.

Analysis: Calculated for $C_{12}H_{15}ClFNO$: C, 59.14; H, 6.20; N, 5.75; Found: C, 59.40; H, 6.20; N, 5.73.

PREPARATION 3

4-(4-Bromobenzoyl)piperidine Hydrochloride 4-(4-Bromobenzoyl)piperidine hydrochloride, m.p. 205° C. (dec.) was prepared according to the procedures of Preparations 1 and 2.

Analysis: Calculated for $C_{12}H_{15}BrClNO$: C, 47.31; N, 4.96; N, 4.60; Found: C, 47.89; H, 5.18; N, 4.59.

PREPARATION 4

4-(4-Chlorobenzoyl)piperidine Hydrochloride 4-(4-Chlorobenzoyl)piperidine hydrochloride, m.p. 233°–235° C., was prepared according to the procedures of Preparations 1 and 2.

Analysis: Calculated for $C_{12}H_{15}Cl_2NO$: C, 55.40; H, 5.81; N, 5.38; Found: C, 55.49; H, 5.84; N, 5.43.

PREPARATION 5

4-(3-Trifluoromethylbenzoyl)piperidine Hydrochloride 4-(3-Trifluoromethylbenzoyl)piperidine hydrochloride, m.p. 196°–198° C. was prepared according to the procedures of Preparations 1 and 2.

Analysis: Calculated for $C_{13}H_{15}ClF_3NO$: C, 53.16; H, 4.81; N, 4.77; Found: C, 53.25; H, 4.19; N, 4.75.

PREPARATION 6

4-Benzoylpiperidine Hydrochloride

4-Benzoylpiperidine hydrochloride, m.p. 223°-225° C. was prepared according to Preparations 1 and 2.

Analysis: Calculated for $C_{12}H_{16}NOCl$: C, 63.85; H, 7.15; N, 6.21; Found: C, 64.17; H, 7.16; N, 6.17.

PREPARATION 7

4-(4-Fluorobenzoyl)-1-(3-hydroxypropyl)piperidine

A mixture of 60.9 g. (0.293 mole) of 4-(4-fluorobenzoyl)piperidine, 46.0 g. (0.31 mole) of 3-bromopropanol and 41.4 g. (0.30 mole) of anhydrous potassium carbonate in 750 ml. of 1-butanol was stirred at reflux for 15 hours. The mixture was filtered, the filtrate concentrated under vacuum and the residual oil was dissolved in acid solution and extracted with benzene. After discarding the benzene layer, the aqueous acid layer was made basic and extracted with chloroform. The chloroform extracts were dried over anhydrous sodium sulfate, the mixture filtered and the filtrate concentrated under vacuum. Anhydrous ether was added to the oily residue and the oil crystallized. The solid which weighed 57.0 g. was washed with ether and filtered. Upon recrystallizing from isopropanol and isopropyl ether, 38.5 g. (48.5%) of product was obtained. A portion (4.0 g.) was recrystallized from petroleum ether to give 2.4 g. of product melting at 105°-110° C.

Analysis: Calculated for $C_{15}H_{20}FNO_2$: C, 67.90; H, 7.60; N, 5.28; Found: C, 68.02; H, 7.55; N, 5.37.

PREPARATION 8

3-[4-(4-Fluorobenzoyl)piperidino]propyl Chloride

Thionyl chloride (38.7 g., 0.376 mole) was added dropwise to a stirred solution of 4-p-fluorobenzoyl-1-(3-hydroxy)propylpiperidine (43.1 g., 0.163 mole) in 400 ml. chloroform at room temperature. After the addition was complete the reaction mixture was stirred at room temperature an additional 16 hr. The chilled mixture was treated with 125 ml. of 6N sodium hydroxide solution added dropwise. The chloroform solution was separated, washed with water, and dried over magnesium sulfate. Removal of the solvent under reduced pressure gave 42.7 g. crude product (92% yield) which crystallized on cooling. Recrystallization from isooctane gave 25.3 g. of pure product, m.p. 66.5°-68.5° C.

Analysis: Calculated for $C_{15}H_{19}NOFCl$: C, 63.49; H, 6.75; N, 4.94; Found: C, 63.49; H, 6.86; N, 4.81.

PREPARATION 9

ω-(4-Benzoylpiperidino)alkyl halides which may be prepared according to the procedures of Preparations 1-8 include:

3-[4-(4-bromobenzoyl)piperidino]propyl chloride,
3-[4-(3-trifluoromethylbenzoyl)piperidino]propyl chloride,
3-[4-(4-chlorobenzoyl)piperidino]propyl chloride,
3-(4-benzoylpiperidino)propyl chloride,
4-[4-(4-fluorobenzoyl)piperidino]butyl chloride, and
2-[4-(4-fluorobenzoyl)piperidino]ethyl chloride.

EXAMPLE 1

7-Chloro-1-{3-[4-(4-fluorobenzoyl)piperidino]propyl}-5-(2-fluorophenyl)-1,2-dihydro-2H-1,4-benzodiazepin-2-one Fumarate Hydrate In a nitrogen atmosphere 7-chloro-5-(2-fluorophenyl)-1,2-dihydro-2H-1,4-benzodiazein-2-one (10 g., 0.0347 mole) in 60 ml. of tetrahydrofuran was added dropwise to a stirring suspension of sodium hydride (1.9 g. 57% oil dispersion, 0.045 mole) in 100 ml. tetrahydrofuran. When the addition was complete the reaction mixture was stirred at room temperature for two hours and then at 50° C. for 0.5 hr. 3-[4-(4-Fluorobenzoyl)piperidino]propyl chloride (10.0 g., 0.0355 mole) in 30 ml. tetrahydrofuran was then added dropwise. After stirring 18 hr. at room temperature 20 ml. of water was added slowly to decompose unreacted sodium hydride. The reaction mixture was filtered and concentrated to give 14.3 g. crude solid. The free base was chromatographed on silica gel. The product obtained from chromatographing the mixture was converted to the fumarate salt which analyzed as the monohydrate.

Analysis: Calculated for $C_{34}H_{33}N_3O_7F_2Cl$: C, 61.03; H, 4.97; N, 6.28; Found: C, 61.09; H, 4.99; N, 6.21.

EXAMPLE 2

When in the procedure of Example 1,3-[4-(4-fluorobenzoyl)piperidino]propyl chloride is replaced by an equal molar amount of 3-[4-(4-bromobenzoyl)piperidino]propyl chloride,
3-[4-(3-trifluoromethylbenzoyl)piperidino]propyl chloride,
3-[4-(4-chlorobenzoyl)piperidino]propyl chloride.
3-(4-benzoylpiperidino)propyl chloride,
4-[4-(4-fluorobenzoyl)piperidino]butyl chloride,
2-[4-(4-fluorobenzoyl)piperidino]ethyl chloride, there are obtained 7-chloro-1-{3-[4-(4-bromobenzoyl)piperidino]propyl}-5-(2-fluorophenyl)-1,2-dihydro-2H-1,4-benzodiazepin-2-one,
7-chloro-1-{3-[4-(3-trifluoromethylbenzoyl)piperidino]propyl}-5-(2-fluorophenyl)-1,2-dihydro-2H-1,4-benzodiazepin-2-one,
7-chloro-1-{3-[4-(4-chlorobenzoyl)piperidino]propyl}-5-(2-fluorophenyl)-1,2-dihydro-2H-1,4-benzodiazepin-2-one,
7-chloro-1-[3-(4-benzoylpiperidine)propyl]-5-(2-fluorophenyl)-1,2-dihydro-2H-1,4-benzodiazepin-2-one,
7-chloro-1-{4-[4-(4-fluorobenzoyl)piperidino]butyl}-5-(2-fluorophenyl)-1,2-dihydro-2H-1,4-benzodiazepin-2-one, and
7-chloro-1-{2-[4-(4-fluorobenzoyl)piperidino]ethyl}-5-(2-fluorophenyl)-1,2-dihydro-2H-1,4-benzodiazepin-2-one.

EXAMPLE 3

7-Chloro-1-{3-[4-(4-fluorobenzoyl)piperidino]propyl}-5-phenyl-1,2-dihydro-4H-1,4-benzodiazepin-2-one.

Using the method of Example 1, 7-chloro-5-phenyl-1,2-dihydro-2H-1,4-benzodiazepin-2-one and 3-[4-(4-fluorobenzoyl)piperidino]propyl chloride are mixed and reacted together to give 7-chloro-1-{3-[4-(4-fluorobenzoyl)piperidino]propyl}-5-phenyl-1,2-dihydro-2H-1,4-benzodiazepin-2-one.

FORMULATION AND ADMINISTRATION

Effective quantities of any of the foregoing pharmacologically active compounds of Formula I may be administered to a living animal body for therapeutic purposes according to usual modes of aministration and in usual forms such as orally in solutions, emulsions, suspensions, pills, tablets and capsules in pharmaceutically acceptable carriers and parenterally in the form of sterile solutions.

For the parenteral administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 25, 50, or 100 milligrams. Five to 50 milligrams appears optimum per unit dose or usual broader ranges appear to be one to 500 milligrams per unit dose. Daily dosages should preferably range from 10 mg. to 100 mg. The active ingredients of the invention may be combined with other pharmacologically active agents as stated above. It is only necessary that the active ingredient constitute an effective amount, i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician or veterinarian.

The following formulations are representative for all of the pharmacologically active compounds of this invention.

FORMULATIONS

(1) Capsules

Capsules of 5 mg., 10 mg., 25 mg., and 50 mg. of active ingredient per capsule are prepared. With the higher amounts of active ingredient, reduction may be made in the amount of lactose.

| Typical blend for encapsulation | Per Capsule, mg. |
| --- | --- |
| Active ingredient, as salt | 5 |
| Lactose | 259 |
| Starch | 126 |
| Magnesium stearate | 4 |
| Total | 394 |

Additional capsule formulations preferably contain a higher dosage of active ingredient and are as follows:

| Ingredients | 100 mg. per Capsule | 250 mg. per Capsule | 500 mg. per Capsule |
| --- | --- | --- | --- |
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selected active ingredient with lactose, starch, and magnesium stearate and encapsulate the blend.

(2) Tablets

A typical formulation for a tablet containing 5.0 mg. of active ingredient per tablet follows. The formulation may be used for other strengths of active ingredient by adjustment of weight of dicalcium phosphate.

|  | Per Tablet, mg. |
| --- | --- |
| 1. Active ingredient | 5.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 202.0 |

Uniformly blend 1, 2, 4 and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and compressed.

| (3) Injectable - 2% sterile solution | Per cc |
| --- | --- |
| Active ingredient     mg. | 20 |
| Preservative, e.g., chlorobutanol, wt./vol... percent | 0.5 |
| Water for injection, q.s. | |

Prepare solution, clarify by filtration, fill into vials, seal and autoclave.

What is claimed is:

1. A compound selected from 1,5-disubstituted-1,2-dihydro-2H-1,4-benzodiazepin-2-ones having the formula:

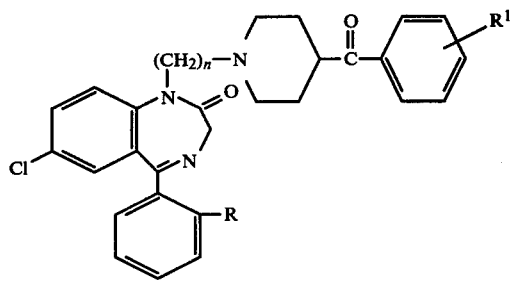

wherein;
R is hydrogen or fluorine,
$R^1$ is hydrogen, fluoro, chloro, bromo or trifluoromethyl,
n is a positive integer from 2 to 4 inclusive, and
non-toxic pharmaceutically acceptable acid addition salts thereof.

2. A compound of claim 1 which is 7-chloro-1-{3-[4-(4-fluorobenzoyl)piperidino]propyl}-5-(2-fluorophenyl)-1,2-dihydro-2H-1,4-benzodiazepin-2-one.

3. A compound of claim 2 in the form of a pharmaceutically acceptable acid addition salt.

4. 7-Chloro-1-{3-[4-(4-fluorobenzoyl)piperidino]propyl}-5-(2-fluorophenyl)-1,2-dihydro-2H-1,4-benzodiazepin-2-one fumarate monohydrate.

5. A pharmaceutical composition useful for its antianxiety effect comprising a pharmaceutically effective amount of a (a) 1,5-disubstituted-1,2-dihydro-2H-1,4-benzodiazepin-2-one selected from those having the formula:

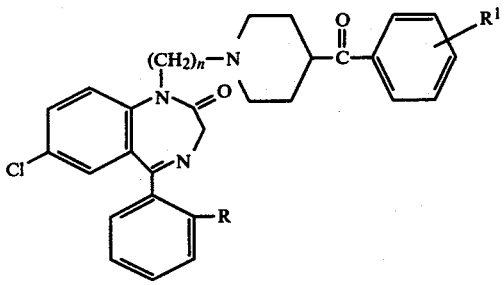

wherein:
R is hydrogen or fluorine,
R[1] is hydrogen, fluoro, chloro, bromo or trifluoromethyl,
n is a positive integer from 2 to 4 inclusive, and
(b) a pharmaceutically acceptable carrier therefor.

6. An anti-anxiety composition as defined in claim 5 wherein the compound is in the form of a pharmaceutically acceptable acid addition salt.

7. An anti-anxiety composition as defined in claim 6 wherein the compound is present in an amount of from 5 to 500 milligrams.

8. An anti-anxiety composition as defined in claim 7 wherein the compound is 7-chloro-1-{3-[4-(4-fluorobenzoyl)piperidino]propyl}-5-(2-fluorophenyl)-1,2-dihydro-2H-1,4-benzodiazepin-2-one.

9. A method for treating anxiety in a host comprising administering to a host suffering from anxiety an effective amount of a compound selected from those having the formula:

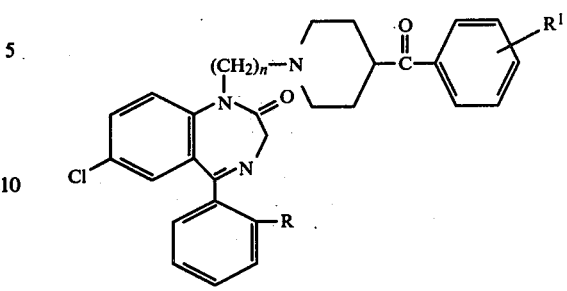

wherein;
R is hydrogen or fluorine,
R[1] is hydrogen, fluoro, chloro, bromo or trifluoromethyl,
n is a positive integer from 2 to 4 inclusive.

10. A method according to claim 9 wherein the compound is in the form of a pharmaceutically acceptable acid addition salt.

11. A method according to claim 10 wherein the compound is administered together with a pharmaceutically acceptable carrier therefor and in an amount of about one to 500 milligrams.

12. A method according to claim 11 wherein the compound is 7-chloro-1-{3-[4-(4-fluorobenzoyl)-piperidino]propyl}-5-(2-fluorophenyl)-1,2-dihydro-2H-1,4-benzodiazepin-2-one.

* * * * *